United States Patent [19]

Reese et al.

[11] 4,117,853

[45] Oct. 3, 1978

[54] FILM-FORMING VINYL ACETATE COPOLYMERIZATES IN AN IMPROVED PROCESS FOR SETTING HAIR AND AS HAIR SETTING AGENTS

[75] Inventors: Günter Reese, Dusseldorf; Hermann Kroke, Erkrath-Unterbach; Fanny Scheuermann, Dusseldorf, all of Fed. Rep. of Germany

[73] Assignee: Henkel Kommanditgesellschaft auf Aktien, Dusseldorf-Holthausen, Fed. Rep. of Germany

[21] Appl. No.: 833,142

[22] Filed: Sep. 14, 1977

Related U.S. Application Data

[63] Continuation-in-part of Ser. No. 627,102, Oct. 30, 1975, abandoned.

[30] Foreign Application Priority Data

Nov. 12, 1974 [DE] Fed. Rep. of Germany ....... 2453629

[51] Int. Cl.$^2$ .......................... A45D 7/00; A61K 7/11
[52] U.S. Cl. ....................................... 132/7; 8/127.51;
260/29.6 TA; 260/33.4 R; 260/33.8 R;
424/DIG. 1; 424/DIG. 2; 424/47; 424/71;
424/78; 424/81
[58] Field of Search ................. 424/DIG. 1, DIG. 2,
424/47, 71, 78, 81; 132/7; 8/127.51; 260/29.6
TA, 33.4 R, 33.8 R

[56] References Cited

U.S. PATENT DOCUMENTS

| | | | |
|---|---|---|---|
| 3,716,633 | 2/1973 | Viout et al. | 424/47 |
| 3,723,616 | 3/1973 | Erlemann et al. | 424/47 |
| 3,925,542 | 12/1975 | Viout et al. | 424/47 |

Primary Examiner—Albert T. Meyers
Assistant Examiner—Vera C. Clarke
Attorney, Agent, or Firm—Hammond & Littell

[57] ABSTRACT

An improvement in the process of setting hair comprising applying a film of a vinyl acetate copolymerizate consisting essentially of (a) from 65% to 80% by weight of vinyl acetate units,
(b) from 10% to 20% by weight of units of a maleic acid diester with a straight-chained alkanol-1 having from about 8 to 10 carbon atoms,
(c) from 5% to 20% by weight of units of a mono-olefinically unsaturated ester having from 6 to 8 carbon atoms and a hydrophilic group, and
(d) from 3% to 10%, particularly 7%, by weight of crotonic acid and salts thereof, to the hair after setting the same; and hair setting agents in the form of hair sprays and setting lotions containing up to 10% by weight of said vinyl acetate copolymerizate and/or salts thereof.

15 Claims, No Drawings

# FILM-FORMING VINYL ACETATE COPOLYMERIZATES IN AN IMPROVED PROCESS FOR SETTING HAIR AND AS HAIR SETTING AGENTS

REFERENCE TO PRIOR APPLICATIONS

This is a continuation-in-part of our copending application Ser. No. 627,102, filed Oct. 30, 1975, and now abandoned.

RELATED ART

Film-forming substances, for use in hairsprays, must fulfill a large number of different requirements, particularly:

(1) They must be highly soluble in the solvents used, particularly in low molecular weight aliphatic alcohols or lower alkanols, such as ethanol and isopropanol.

(2) The solutions must be miscible with the propellants, such as Freon (registered trademark), which are used, without causing turbidity or precipitation.

(3) The viscosity of the film formers must not be too high, in order to ensure satisfactory atomization during spraying.

(4) The film produced should adhere satisfactorily to hair and must not flake off in the form of dust or scales when subject to mechanical stresses such as combing.

(5) The film should be clearly transparent and lustrous.

(6) The film should be flexible, but at the same time should have sufficient strength and elasticity to fix the coiffure.

(7) The film should not be sticky even in the case of high atmospheric humidity.

(8) The film should be capable of being removed by simple means, such as a normal shampoo.

(9) The film should have a satisfactory antistatic effect.

If these film-forming substances are also required for use in setting lotions, there is an additional essential requirement, i.e.:

(10) Their alcoholic solutions should be capable of being diluted with water to a virtually unlimited extent, after, if required, complete or partial neutralization of the hydrophilic groups of the film formers, and without the occurrence of turbidity or precipitations.

It is very difficult matter to find substances which adequately meet all these requirements. The requirements of points 7, 8 and 10 give rise to special difficulties since, in general, those substances which are easy to remove and whose solutions can be largely diluted with water, are usually unsatisfactory at a high relative atmospheric humidity, since they become sticky owing to their high degree of solubility in water.

OBJECTS OF THE INVENTION

An object of this invention is to provide hair setting agents in the form of hairsprays and setting lotions containing film-forming substances which largely fulfill all the aforesaid requirements.

Another object of the present invention is the development of a hair setting composition comprising from 0.5% to 10% by weight of a film-forming vinyl acetate copolymerizate having a K-value of from 20 to 70, preferably from 30 to 52, of monomer units consisting essentially of (a) from 65% to 80% by weight of vinyl acetate units, (b) from 10% to 20% by weight of units of a maleic acid diester with straight-chained primary alcohols selected from the group consisting of n-octanol-1, n-decanol-1 and mixtures thereof, (c) from 5% to 20% by weight of units of a mono-olefinically unsaturated ester copolymerizable with vinyl acetate and having from 6 to 8 carbon atoms and a hydrophilic group selected from the group consisting of carboxyl groups, hydroxyl groups and keto groups, and (d) from 3% to 10% by weight of crotonic acid units, and the salts thereof, and the remainder, the customary hair setting auxiliaries, solvents and optionally propellants.

A further object of the present invention is the development, in the process of setting hair comprising arranging the hair in the desired configuration and applying a thin film of a film-forming substance on the so-arranged hair, the improvement consisting of utilizing a vinyl acetate copolymerizate having a K-value of from 20 to 70, preferably from 30 to 52, of monomer units consisting essentially of (a) from 65% to 80% by weight of vinyl acetate units, (b) from 10% to 20% by weight of units of a maleic acid diester with straight-chained primary alcohols selected from the group consisting of n-octanol-1, n-decanol-1 and mixtures thereof, (c) from 5% to 20% by weight of units of a mono-olefinically unsaturated ester copolymerizable with vinyl acetate and having from 6 to 8 carbon atoms and a hydrophilic group selected from the group consisting of carboxyl groups, hydroxyl groups and keto groups, and (d) from 3% to 10% by weight of crotonic acid units, and salts thereof, as said film-forming substance.

These and other objects of the present invention will become more apparent as the description thereof proceeds.

DESCRIPTION OF THE INVENTION

Unexpectedly, it was discovered that the said requirements for hair setting agents are substantially met by hair setting agents in the form of a hairspray or a setting lotion and which contain, as film-forming substances, copolymerizates having a K-value of from 20 to 70, preferably from 30 to 52, of monomer units consisting of (a) from 65% to 80% by weight of vinyl acetate units, (b) from 10% to 20% by weight of units of a maleic acid diester with a straight-chain alkanol-1 having 8 or 10 carbon atoms or with a mixture of such alkanols, (c) from 5% to 20% by weight of units of a mono-olefinically unsaturated ester having 6, 7 or 8 carbon atoms and having a hydrophilic group, and (d) from 3% to 10%, preferably 7%, by weight of crotonic acid units, or salts of these copolymers with alkali metals, ammonia or amines or alkanolamines having 2 to 8 carbon atoms.

More particularly, the present invention relates to a hair setting composition comprising from 0.5% to 10% by weight of a film-forming vinyl acetate copolymerizate having a K-value of from 20 to 70, preferably from 30 to 52, of monomer units consisting essentially of (a) from 65% to 80% by weight of vinyl acetate units, (b) from 10% to 20% by weight of units of a maleic acid diester with straight-chained primary alcohols selected from the group consisting of n-octanol-1, n-decanol-1 and mixtures thereof, (c) from 5% to 20% by weight of units of a monoolefinically unsaturated ester copolymerizable with vinyl acetate and having from 6 to 8 carbon atoms and a hydrophilic group selected from the group consisting of carboxyl groups, hydroxyl groups and keto groups, and (d) from 3% to 10% by weight of crotonic acid units, and salts thereof, and the remainder, the customary hair setting auxiliaries, solvents and optionally propellants, as well as, in the process of setting hair comprising arranging the hair in the desired configuration and applying a thin film of a film-forming substance on the so-arranged hair, the improvement consisting of utilizing a vinyl acetate copolymerizate of monomer units consisting essentially of (a) from 65% to 80% by weight of vinyl acetate units, (b) from 10% to 20% by weight of units of a maleic acid diester with straight-chained primary alcohols selected from the group consisting of n-octanol-1, n-decanol-1 and mixtures thereof, (c) from 5% to 20% by weight of units of a monoolefinically unsaturated ester copolymerizable with vinyl acetate and having from 6 to 8 carbon atoms and a hydrophilic group selected from the group consisting of carboxyl groups, hydroxyl groups and keto groups, and (d) from 3% to 10% by weight of crotonic acid units, and salts thereof, as said film-forming substance.

These copolymers and their salts are soluble in alcoholic solutions, and such solutions can — after complete or partial neutralization — surprisingly, be diluted with water to a relatively large extent. In some cases, the alcoholic solutions are miscible with water in all proportions.

The copolymers or their salts, to be used in the hair setting compositions in accordance with the invention are not the subject matter of the present application. These copolymers and the processes for their production are described and claimed in U.S. patent application Ser. No. 627,103, filed Oct. 30, 1975, now U.S. Pat. No. 4,048,192, entitled "Water-Dilutable Vinyl Acetate Copolymers." The copolymers of the invention may be manufactured by conventional polymerization methods, for example, in bulk, in solution, in suspension, or in emulsion. Each of the monomers (a) to (d) may be wholly introduced into the polymerization medium prior to the commencement of polymerization, or may be wholly metered in during polymerization, or may be partially introduced initially and partially metered in.

The ratio of the four comonomers as specified above is important for those solubility properties of the copolymers. The presence of the maleic acid diester with a straight chain alkanol-1 having 8 and/or 10 carbon atoms also appears to be important for solubility. The presence of component (c) is also important and cannot be replaced by, for example, more crotonic acid without deterioration in the solubility of the copolymer, notwithstanding that both components are hydrophilic.

Component (b) of the copolymer according to the invention consists of units of a maleic acid diester preferably with an Alfol ® alcohol having 8 or 10 carbon atoms or with a mixture of such alcohols. These diesters may be manufactured from maleic acid and an Alfol ® alcohol having 8 or 10 carbon atoms or a mixture of such alcohols, such as Alfol-8 ®, Alfol-10 ® and Alfol 810 ®. Alfol ® alcohols are alcohols produced industrially by the polymerization of ethylene on aluminum to give aluminum alkanes, with subsequent oxidation to give aluminum alkoxides, and then hydrolysis to form the alcohols. They are primary, straight-chained, aliphatic alcohols and are in the form of colorless liquids. The alcohols with a chain length of 8 or 10 carbon atoms or mixtures thereof are used according to the invention. However, other normal or straight chained primary alkanols having 8 to 10 carbon atoms can be used for esterification of maleic acid, such as n-octanol-1, n-decanol-1 and mixtures thereof.

Component (c) consists of units of one or more monoolefinically unsaturated esters copolymerizable with vinyl acetate and having 6 to 8 carbon atoms and a hydrophilic group. The hydrophilic group is advantageously a hydroxy or carboxy group, but may be another hydrophilic group, for example, a keto group. It may be attached to either the alcohol or acid moiety of the ester. The double bond may also be in either the acid or alcohol moiety of the ester. Examples of such esters are monoalkyl maleates having 6 to 8 carbon atoms, e.g., monoethyl maleate and monobutyl maleate; hydroxyalkyl acrylates having 6 to 8 carbon atoms, e.g., hydroxypropyl acrylate and hydroxybutyl acrylate; and hydroxyalkyl methacrylates, e.g., hydroxypropyl methacrylate. Mixtures of such esters may also be used.

Component (d), namely, crotonic acid units, is advantageously present in an amount of from 3% to 7% by weight.

Polymerization may be initiated by a free-radical-forming initiator or polymerization catalyst, which may be either water-soluble or monomer-soluble depending on the type of polymerization. Suitable free-radical-forming initiators are those that are suitable for initiating the homopolymerization of vinyl acetate at temperatures of from 30° to 140° C., and especially peroxy compounds are preferred.

The amount of initiator used is suitably within the range of from 0.01% to 1% by weight, preferably from 0.1% to 0.6% by weight, calculated relative to the total weight of monomers. Polymerization is advantageously carried out at a temperature of from 30° to 140° C., preferably from 50° to 120° C. The degree of polymerization may be adjusted within a wide range, in known manner, by means of a molecular-weight regulator. By suitable use of molecular weight regulators, products having K-values within the range of from 20 to 70, preferably from 30 to 52, can generally be obtained. The K-value is a measure of the degree of polymerization, and is calculated from the relative viscosity of the product. The K-values given herein are calculated from the relative viscosities as determined in a 1% by weight solution in acetone at 20° C. with a Ubbelohde capillary viscometer (Fikentscher, Cellulosechemie 13, 1932, pp. 58 ff).

A preferred method for the manufacture of the copolymers is by bulk polymerization in the presence of a monomer-soluble peroxy compound, especially a dialkyl peroxydicarbonate, and of a molecular weight regulator at a temperature of from 30° to 140° C.

The copolymers may be neutralized, or partially neutralized, by means of either an organic or an inorganic base to obtain the corresponding salts. Preferably, before neutralization or partial neutralization, the copolymers according to the invention are dissolved in at least one water-miscible organic solvent, such as the water-miscible lower alkanols. Suitable inorganic bases for neutralization are the alkali metal hydroxides, such as sodium hydroxide and potassium hydroxide preferably in solution, for example, in a lower alkanol, or ammonia. Suitable organic bases are amines, preferably having from 2 to 8 carbon atoms and optionally substituted by a hydroxy group (namely, amino alcohols). These are amines having from 2 to 8 carbon atoms selected from the group consisting of alkylamines, alkylolamines, alkylenediamines, dialkylenetriamines, alkylaminoalkanols, aminoalkyleneglycols, etc., for example, dimethylamine, ethylamine, diethylamine, aminoethylamine, ethanolamine, isopropanolamine, 2-amino-2-methyl-propan-1-ol, 2-amino-2-methyl-propane-1,3-diol, and diethylaminoethanol; 2-amino-2-propane-1,3-diol is preferred. For the purposes of neutralization, the bases are generally used in quantities of 50% to 150% of the quantity theoretically required for neutralization. Neutralization of the copolymers with 90% of the quantity theoretically required for neutralization has proved to be most advantageous for the use of the salts as film formers in the hair setting compositions in accordance with the invention.

The hair setting compositions in accordance with the invention can be provided in the form of a hairspray. For this purpose, the copolymers to be used, or preferably their salts, particularly with 2-amino-2-methyl-propane-1,3-diol, are dissolved in low-molecular-weight aliphatic alcohols, particularly water-miscible lower alkanols, such as ethanol and isopropanol. The propellants employed are advantageously the commercially available halogenated hydrocarbons having 1 or 2 carbon atoms such as trichloromonofluoromethane, dichlorodifluoromethane or dichlorotetrafluoroethane. One or other of the said propellant compounds is chosen, depending upon the desired pressure which is to prevail in the aerosol spray can. Alternatively, it is frequently advantageous to use a mixture of different propellants.

In order to manufacture the hair setting compositions, in accordance with the invention, in the form of aerosol spray preparations, it is advantageous to use solutions which contain up to approximately 10% by weight (relative to the total mixture including propellant) of the copolymer, or its salts, to be used as film formers. The quantity of the film former is generally 0.5% to 5% by weight based on the total mixture including propellant. The aliphatic alcohols serving as solvents for the copolymers or their salts, constitute approximately 25% to 40% by weight of the total mixture, while approximately 60% to 75% by weight of the total mixture is allotted to the halogenated hydrocarbon propellants.

Alternatively, the hair setting compositions in accordance with the invention can comprise a setting lotion such as a water-waving lotion. For this purpose, the salts of the copolymers, particularly their salts, especially with 2-amino-2-methyl-propane-1,3-diol, which have been obtained by neutralization with preferably 90% of the quantity of bases theoretically required for neutralization, are dissolved in 20% to 50% by weight of water-miscible lower alkanols and mixed with the remainder up to 100% of water. The quantity of the film formers in such lotions is generally between 0.5% to 5% by weight, preferably 1% to 3% by weight based on the total lotion.

The hair setting agents in accordance with the invention may contain, in addition to the film formers, solvents and propellants, conventional additives such as plasticizers, perfumes, coloring matter, agents for imparting luster to the hair, evaporation retarders and other auxiliary agents customary in cosmetics.

In general, the hair setting compositions of the invention comprise a hair setting composition consisting essentially of from 0.5% to 10% by weight of a film-forming vinyl acetate copolymerizate having a K-value of from 20 to 70, preferably from 30 to 52, of monomer units consisting essentially of (a) from 65% to 80% by weight of vinyl acetate units,
(b) from 10% to 20% by weight of units of a maleic acid diester with straight-chained primary alcohols selected from the group consisting of n-octanol-1, n-decanol-1 and mixtures thereof,
(c) from 5% to 20% by weight of units of a mono-olefinically unsaturated ester copolymerizable with vinyl acetate and having from 6 to 8 carbon atoms and a hydrophilic group selected from the group consisting of carboxyl groups, hydroxyl groups and keto groups, and
(d) from 3% to 10% by weight of crotonic acid units; in the form wherein at least 50% of the acid groups therein are neutralized, from 20% to 50% by weight of water-miscible lower alkanols,
from 40% to 79.5% by weight of a member selected from the group consisting of water, a halogenated hydrocarbon having 1 to 2 carbon atoms, and mixtures thereof, and
from 0 to 5% by weight of at least one of: plasticizers, perfumes, coloring agents, hair lustering agents, evaporation retarders.

The advantage obtainable by means of the hair setting compositions in accordance with the invention resides in the fact that they produce resilient films on the hair which are insensitive to high atmospheric humidity and impart a high luster to the hair. The films have no tendency to flake off when combing and brushing the hair, although they can be readily removed by means of a normal shampoo. The films produced by the hair setting compositions in accordance with the invention counteract, to a certain extent, the static electricity charging of the hair. Furthermore, it is to be emphasized that the use of the alcoholic solutions of the film formers in setting lotions is promoted by the fact that they are capable of being diluted in water.

This invention will now be further described by means of the following Examples which are not limitative in any respect.

EXAMPLES

The production of some of the copolymers to be used in accordance with the invention will be described in the first instance.

The amounts of peroxy compounds given in grams below are the amounts of a 20% solution of the respective compounds.

PRODUCT A 250 gm of vinyl acetate, 46 gm of di-Alfol-810 ® maleate, 10 gm of monobutyl maleate, 8 gm of crotonic acid, 9.5 gm of acetaldehyde, and 1 gm of diisopropyl peroxydicarbonate, were introduced into a 2-liter reaction vessel fitted with a stirrer, reflux condenser, and nitrogen inlet-tube. Alfol-810 ® is a mixture of predominantly n-octanol-1 and n-decanol-1. The mixture was heated, with stirring, while passing a slight stream of nitrogen, until reflux commenced (64° C.). Ten minutes after the commencement of reflux, the dosing in of a mixture of 334 gm of vinyl acetate, 50 gm of di-Alfol-810 ® maleate, 70 gm of monobutyl maleate, 32 gm of crotonic acid, and 4 gm of diisopropyl peroxydicarbonate was started. The dosing in was at a steady rate and was complete after 5 hours, during which time the temperature was maintained at 64° C. Polymerization was then continued for a further 2 to 2½ hours, during which time the temperature was gradually raised to 82° C. During this time also, a one-gram portion of diisopropyl peroxydicarbonate was added every 30 minutes. The cessation of reflux indicated the end of the reaction. The small residue of monomers was distilled off to leave a clear colorless copolymer melt.

The copolymer had the following weight composition:
vinyl acetate — 73%
di-Alfol-810 ® maleate — 12%
monobutyl maleate — 10%
crotonic acid — 5%

It had a K-value of 30 (determined as a 1% solution in acetone at 20° C.) and an acid number of 68 mg KOH/gm.

PRODUCT B

Polymerization was carried out in an analogous manner to Product A. 250 gm of vinyl acetate, 60 gm of di-Alfol-810 ® maleate, 16 gm of monobutyl maleate, 20 gm of crotonic acid, 6.5 gm of acetaldehyde, and 1 gm of diisopropyl peroxydicarbonate were initially introduced, and were heated until reflux commenced (68° C.). After 10 minutes, the remainder of the components were dosed in over a period of 5 hours. These consisted of 334 gm of vinyl acetate, 60 gm of di-Alfol-810 ® maleate, 24 gm of monobutyl maleate, 36 gm of crotonic acid, and 5 gm of diisopropyl peroxydicarbonate.

The product was a clear colorless polymer of the following composition:
vinyl acetate — 73%
di-Alfol-810 ® maleate — 15%
monobutyl maleate — 5%
crotonic acid — 7%

It had a K-value of 37, and an acid number of 63.4 mg KOH/gm.

PRODUCT C

Polymerization was again carried out analogously to Product A. 250 gm of vinyl acetate, 50 gm of di-Alfol-810 ® maleate, 10 gm of hydroxypropyl acrylate, 8 gm of crotonic acid, 5.5 gm of acetaldehyde, and 1 gm of diisopropyl peroxydicarbonate were initially introduced and heated until reflux commenced at about 67° C. After 10 minutes the remainder of the components were dosed in over a period of 6 hours. These consisted of 310 gm of vinyl acetate, 70 gm of di-Alfol-810 ® maleate, 70 gm of hydroxypropyl acrylate, 32 gm of crotonic acid and 4 gm of diisopropyl peroxydicarbonate. Two and one-half hours after completion of the dosing in, at an inner temperature of 90° C., polymerization was terminated.

The colorless clear copolymer obtained had the following weight composition:
vinyl acetate — 70%
di-Alfol-810 ® maleate — 15%
hydroxypropyl acrylate — 10%
crotonic acid — 5%

It had a K-value of 36 and an acid number of 35 mg KOH/gm.

PRODUCT D

Polymerization was again carried out as in Example 1. 220 gm of vinyl acetate, 30 gm of di-Alfol-810 ® maleate, 20 gm of monobutyl maleate, 10 gm of crotonic acid, 1.6 gm of acetaldehyde, and 1 gm of diisopropyl peroxydicarbonate were initially introduced. Ten minutes after reflux had begun at a temperature of 65° C., the remainder of the components were dosed in over a period of 5 hours. These consisted of 284 gm of vinyl acetate, 50 gm of di-Alfol-810 ® maleate, 140 gm of monobutyl maleate, 46 gm of crotonic acid, and 4 gm of diisopropylperoxydicarbonate. Polymerization was complete 3 hours after the completion of the introduction of the monomers when the temperature had reached 85° C.

The clear colorless polymer had the following weight composition:
vinyl acetate — 63%
di-Alfol-810 ® maleate — 10%
monobutyl maleate — 20%
crotonic acid — 7%

It had a K-value of 52, and an acid number of 113 mg KOH/gm.

In the manner described hereinafter, the copolymers obtained in accordance with the above, particularly in the form of their salts, with alkalis, ammonia, amines, or alkanolamines, can be incorporated in hair setting compositions. It has proved to be advantageous to neutralize the copolymers with approximately 90% of the quantity of bases theoretically required for neutralization, the most suitable base being 2-amino-2-methyl-propanediol-(1,3) with respect to the technical properties of the film formed.

EXAMPLE 1

Hairspray

The following solution was prepared in the first instance:

| | Parts by Weight |
|---|---|
| Product A | 3.0 |
| 2-amino-2-methyl-propane-1,3-diol | 0.34 |
| Methylenechloride | 20.0 |
| Perfume oil | 0.2 |
| Isopropanol | 76.45 |

40 Parts by weight of this solution were introduced into an aerosol container together with 60 parts by weight of a propellant mixture comprising equal parts by weight of trichlorofluoromethane and dichlorodifluoromethane.

The hairspray obtained produced a lustrous nonadhesive film which can be readily removed by washing the hair.

EXAMPLE 2

Hairspray

The following solution served as the starting formulation:

| | Parts by Weight |
|---|---|
| Product B | 4.0 |

-continued

|  | Parts by Weight |
|---|---|
| 2-amino-2-methyl-propane-1,3-diol | 0.43 |
| Methylenechloride | 20.0 |
| Perfume oil | 0.2 |
| Isopropanol | 75.37 |

40 Parts by weight of this solution were introduced into an aerosol container together with 60 parts by weight of a propellant mixture comprising equal parts by weight of trichlorofluoromethane and dichlorodifluoromethane.

The hairspray thus obtained is highly effective with respect to setting the hair and produces a lustrous film which does not become sticky and which can readily be removed by washing.

EXAMPLE 3

Hairspray

The following solution was used for producing the spray:

|  | Parts by Weight |
|---|---|
| Product C | 4.0 |
| Diethylaminoethanol | 0.27 |
| Methylenechloride | 20.0 |
| Perfume oil | 0.2 |
| Ethanol | 75.53 |

40 Parts by weight of the solution obtained were introduced into an aerosol container together with 60 parts by weight of a propellant mixture comprising equal parts by weight of trichlorofluoromethane and dichlorodifluoromethane.

The films obtained with this spray are lustrous, are very effective with respect to setting the hair, are not hygroscopic and can readily be removed by washing.

EXAMPLE 4

Hairspray

The following solution was prepared:

|  | Parts by Weight |
|---|---|
| Product D | 5.0 |
| Isopropanolamine | 0.68 |
| Methylenechloride | 20.0 |
| Perfume oil | 0.2 |
| Isopropanol | 74.12 |

40 Parts by weight of the solution obtained were introduced into an aerosol container together with 60 parts by weight of a propellant mixture comprising equal parts by weight of trichlorofluoromethane and dichlorodifluoromethane.

The spray produced lustrous films which do not become sticky and which impart a high degree of "hold" to the hair and which can be readily removed by washing.

EXAMPLE 5

Hairspray

The following solution served as the starting formulation:

|  | Parts by Weight |
|---|---|
| Product A | 20.0 |
| Diethylamine | 1.6 |
| Perfume oil | 0.2 |
| Ethanol | 78.2 |

25 Parts by weight of the solution were introduced into an aerosol container together with 45 parts by weight of trichlorofluoromethane and 30 parts by weight of dichlorodifluoromethane.

The films produced by this spray are very effective with respect to setting the hair, are lustrous, nonhygroscopic and can be readily removed by washing.

EXAMPLE 6

Water-waving Lotion

The constituents were dissolved in the following quantities for the purpose of producing the lotion:

|  | Parts by Weight |
|---|---|
| Product B | 2.0 |
| 2-amino-2-methyl-propane-1,3-diol | 0.22 |
| Polyglycol 400 | 0.2 |
| Perfume oil | 0.2 |
| Ethanol | 40.0 |
| Water | 57.38 |

Treatment with the lotion renders the hair lustrous and smooth and imparts a satisfactory hold and fullness to the hair.

EXAMPLE 7

Water-waving Lotion

This lotion has the following composition:

|  | Parts by Weight |
|---|---|
| Product A | 3.0 |
| 2-amino-2-methyl-propane-1,3-diol | 0.34 |
| Polyglycol 400 | 0.2 |
| Perfume oil | 0.2 |
| Isopropanol | 35.0 |
| Water | 61.26 |

A durable and lustrous coiffure is obtained by means of this lotion.

EXAMPLE 8

Water-waving Lotion

The constituents were used in the following quantities in order to manufacture the lotion:

|  | Parts by Weight |
|---|---|
| Product D | 1.0 |
| Isopropanolamine | 0.14 |
| Isopropyl myristate | 0.2 |
| Perfume oil | 0.2 |
| Ethanol | 25.0 |
| Water | 73.46 |

The lotion produces lustrous and smooth hair having a high degree of fullness.

EXAMPLE 9

Water-waving Lotion

The lotion was prepared from the following constituents:

|  | Parts by Weight |
|---|---|
| Product C | 2.0 |
| Diethylaminoethanol | 0.14 |
| Polyglycol 400 | 0.2 |
| Catyltrimethylammoniumchloride | 0.02 |
| Perfume oil | 0.2 |
| Isopropanol | 40.0 |
| Water | 57.44 |

Treatment with the above-mentioned lotion imparts to the hair an extremely small tendency to static charging, in addition to a high luster, smoothness and a high degree of fullness.

EXAMPLE 10

Water-waving Lotion

The following constituents were used for preparing the lotion:

|  | Parts by Weight |
|---|---|
| Product A | 2.0 |
| 2-amino-2-methyl-propane-1,3-diol | 0.12 |
| Isopropyl myristate | 0.2 |
| Vegetable extract | 0.2 |
| Albumin hydrolysate | 0.2 |
| Perfume oil | 0.2 |
| Ethanol | 30.0 |
| Water | 66.88 |

The lotion produces a durable coiffure having a beautiful luster and a high degree of smoothness. The film obtained can be readily removed by washing in the same manner as in the case of the aforementioned water-waving lotions.

Alternatively, bases such as sodium hydroxide, potassium hydroxide, ammonia, dimethylamine, ethylamine, diisopropylamine, aminoethylamine, ethanolamine, 2-amino-2-methyl-propan-1-ol, methylaminoethanol, dimethylaminoethanol can be used in the appropriate quantities in accordance with the invention, instead of the bases given in the Examples.

The preceding specific embodiments are illustrative of the practice of the invention. It is to be understood, however, that other expedients known to those skilled in the art, or disclosed herein, may be employed without departing from the spirit of the invention or the scope of the appended claims.

We claim:

1. A hair setting composition consisting essentially of from 0.5% to 10% by weight of a film-forming vinyl acetate copolymerizate having a K-value of from 20 to 70 of monomer units consisting of
    (a) from 65% to 80% by weight of vinyl acetate units,
    (b) from 10% to 20% by weight of units of a maleic acid diester with straight-chained primary alcohols selected from the group consisting of n-octanol-1, n-decanol-1 and mixtures thereof,
    (c) from 5% to 20% by weight of units of a mono-olefinically unsaturated ester copolymerizable with vinyl acetate and having from 6 to 8 carbon atoms and a hydrophilic group selected from the group consisting of carboxyl groups, hydroxyl groups and keto groups, and
    (d) from 3% to 10% by weight of crotonic acid units; in the form wherein at least 50% of the acid groups therein are neutralized,
    from 20% to 50% by weight of water-miscible lower alkanols, and
    from 40% to 79.5% by weight of a member selected from the group consisting of water, a halogenated hydrocarbon having 1 to 2 carbon atoms, and mixtures thereof.

2. The hair setting composition of claim 1 wherein said film-forming vinyl acetate copolymerizate is present in an amount of from 0.5% to 5% by weight, said water is substantially absent and said composition is employed as a hair spray.

3. The hair setting composition of claim 1 wherein said film-forming vinyl acetate copolymerizate is present in an amount of from 0.5% to 50% by weight, at least 40% by weight of said composition is water and said composition is employed as a setting lotion.

4. The hair setting composition of claim 1 wherein said copolymerizate is present in an amount of from 1% to 3% by weight.

5. The hair setting composition of claim 1 wherein said film-forming vinyl acetate copolymerizate is in the form of a salt obtained by neutralization of the copolymer with 90% of the quantity of base theoretically required for neutralization.

6. The hair setting composition of claim 5 wherein said base utilized for said 90% neutralization is 2-amino-2-methyl-propane-1,3-diol.

7. The hair setting composition of claim 1 wherein said film-forming vinyl acetate copolymerizate has a K-value of from 30 to 52.

8. The hair setting composition of claim 1 having a content of from 0 to 5% by weight of perfumes.

9. The hair setting composition of claim 1 wherein the acid groups in said film-forming vinyl acetate copolymerizate are at least 50% neutralized with an amine having from 2 to 8 carbon atoms selected from the group consisting of alkylamines, alkylolamines, alkylenediamines, dialkylenetriamines, alkylaminoalkanols and aminoalkyleneglycols.

10. In the process of setting hair comprising arranging the hair in the desired configuration and applying a thin film of a film-forming substance on the so-arranged hair, the improvement consisting of utilizing, as said film-forming substance, a film-forming vinyl acetate copolymerizate having a K-value of from 20 to 70, of monomer units consisting of
    (a) from 65% to 80% by weight of vinyl acetate units,
    (b) from 10% of 20% by weight of units of a maleic acid diester with straight-chained primary alcohols selected from the group consisting of n-octanol-1, n-decanol-1 and mixtures thereof,
    (c) from 5% to 20% by weight of units of a mono-olefinically unsaturated ester copolymerizable with vinyl acetate and having from 6 to 8 carbon atoms and a hydrophilic group selected from the group consisting of carboxyl groups, hydroxyl groups and keto groups, and
    (d) from 3% to 10% by weight of crotonic acid units, and the salts thereof, in the form wherein at least 50% of the acid groups therein are neutralized.

11. The process of claim 10 wherein, in said film-forming vinyl acetate copolymerizate, said monomer units (d) are present in an amount of from 3% to 7% by weight.

12. The process of claim 10 wherein said film-forming vinyl acetate copolymerizate is in the form of a salt obtained by neutralization of the copolymer with 90% of the quantity of base theoretically required for neutralization.

13. The process of claim 12 wherein said base utilized for said 90% neutralization is 2-amino-2-methylpropane-1,3-diol.

14. The process of claim 10 wherein said film-forming vinyl acetate copolymerizate has a K-value of from 30 to 52.

15. The process of claim 10 wherein the acid groups in said film-forming vinyl acetate copolymerizate are at least 50% neutralized with an amine having from 2 to 8 carbon atoms selected from the group consisting of alkylamines, alkylolamines, alkylenediamines, dialkylenetriamines, alkylaminoalkanols and aminoalkyleneglycols.

* * * * *